United States Patent
Wang et al.

(10) Patent No.: US 7,781,729 B2
(45) Date of Patent: *Aug. 24, 2010

(54) ANALYZING MASS SPECTRAL DATA

(75) Inventors: Yongdong Wang, Wilton, CT (US); Ming Gu, Yardley, PA (US)

(73) Assignee: Cerno Bioscience LLC, Danbury, CT (US)

( * ) Notice: Subject to any disclaimer, the term of this patent is extended or adjusted under 35 U.S.C. 154(b) by 323 days.

This patent is subject to a terminal disclaimer.

(21) Appl. No.: 11/754,305

(22) Filed: May 27, 2007

(65) Prior Publication Data

US 2008/0001079 A1    Jan. 3, 2008

Related U.S. Application Data

(60) Provisional application No. 60/809,135, filed on May 26, 2006.

(51) Int. Cl.
*B01D 59/44* (2006.01)
*H01J 49/00* (2006.01)

(52) U.S. Cl. ............... 250/282; 250/281; 250/283; 250/287; 250/288; 250/289; 250/290; 250/291; 250/292; 702/22; 702/23; 702/31; 702/76; 702/85

(58) Field of Classification Search ......... 250/281–283, 250/287–292; 702/22, 23, 31, 76, 85
See application file for complete search history.

(56) References Cited

U.S. PATENT DOCUMENTS

| | | | |
|---|---|---|---|
| 5,300,771 A | 4/1994 | Labowsky | |
| 5,538,897 A | 7/1996 | Yates, III et al. | |
| 6,118,120 A | 9/2000 | Fenn et al. | |
| 6,983,213 B2 | 1/2006 | Wang | |
| 7,199,363 B2* | 4/2007 | Bateman et al. | 250/287 |
| 2006/0249669 A1* | 11/2006 | Bern | 250/282 |
| 2008/0052011 A1* | 2/2008 | Wang et al. | 702/27 |
| 2008/0302957 A1* | 12/2008 | Wang et al. | 250/282 |
| 2009/0076737 A1* | 3/2009 | Wang et al. | 702/23 |

OTHER PUBLICATIONS

A. L. Yergey et al., De Novo Sequencing of Peptides Using MALDI/TOF-TOF, J. Am. Soc. Mass Spectrom. 2002, vol. 13, pp. 784-791, May 2002.

* cited by examiner

*Primary Examiner*—Jack I Berman
*Assistant Examiner*—Meenakshi S Sahu
(74) *Attorney, Agent, or Firm*—David Aker

(57) ABSTRACT

A method for analyzing data from a mass spectrometer comprising obtaining calibrated continuum spectral data by processing raw spectral data; obtaining library spectral data which has been processed to form calibrated library data; and performing a least squares fit, preferably using matrix operations (equation 1), between the calibrated continuum spectral data and the calibrated library data to determine concentrations of components in a sample which generated the raw spectral data. A mass spectrometer system (FIG. 1) that operates in accordance with the method, a data library of transformed mass spectra, and a method for producing the data library.

64 Claims, 2 Drawing Sheets

ANALYZING MASS SPECTRAL DATA

This application claims priority from U.S. provisional application Ser. No. 60/809,135 filed on May 26, 2006, which is herein incorporated by reference, in its entirety.

CROSS REFERENCE TO RELATED PATENT APPLICATIONS/PATENTS

The entire contents of the following documents are incorporated herein by reference in their entireties:

U.S. Pat. No. 6,983,213; International Patent Application PCT/US2004/013096, filed on Apr. 28, 2004; U.S. patent application Ser. No. 11/261,440, filed on Oct. 28, 2005; International Patent Application PCT/US2005/039186, filed on Oct. 28, 2005; and International Patent Application PCT/US2006/013723, filed on Apr. 11, 2006.

BACKGROUND OF THE INVENTION

1. Field of the Invention

The present invention relates to mass spectrometry systems. More particularly, it relates to mass spectrometry systems that are useful for the analysis of complex mixtures of molecules, including large organic molecules such as proteins or peptides, environmental pollutants, pharmaceuticals and their metabolites, and petrochemical compounds, to methods of analysis used therein, and to a computer program product having computer code embodied therein for causing a computer, or a computer and a mass spectrometer in combination, to affect such analysis.

2. Prior Art

Liquid chromatography interfaced with tandem mass spectrometry (LC/MS/MS) has become a method of choice for protein sequencing (Yates Jr. et al., Anal. Chem. 67, 1426-1436 (1995)). This method involves a few processes including digestion of proteins, LC separation of peptide mixtures generated from the protein digests, MS/MS analysis of the resulting peptides, and database search for protein identification. The key to effectively identify proteins with LC/MS/MS is to produce as many high quality MS/MS spectra as possible to allow for reliable matching during database search. This is achieved by a data-dependent scanning technique in a quadrupole or an ion trap instrument. With this technique, the mass spectrometer checks the intensities and signal to noise ratios of the most abundant ion(s) in a full scan MS spectrum and perform MS/MS experiments when the intensities and signal to noise ratios of the most abundant ions exceed a preset or predetermined threshold. Usually the three most abundant ions are selected for the product ion scans to maximize the sequence information and minimize the time required, as the selection of more than three ions for MS/MS experiments would possibly result in missing other qualified peptides currently eluting from the LC to the mass spectrometer.

The success of LC/MS/MS for identification of proteins is largely due to its many outstanding analytical characteristics. Firstly, it is a quite robust technique with excellent reproducibility. It has been demonstrated that it is reliable for high throughput LC/MS/MS analysis for protein identification. Secondly, when using nanospray ionization, the technique delivers quality MS/MS spectra of peptides at sub-femtomole levels. Thirdly, the MS/MS spectra carry sequence information of both C-terminal and N-terminal ions. This valuable information can be used not only for identification of proteins, but also for pinpointing what post translational modifications (PTM) have occurred to the protein and at which amino acid reside the PTM take place.

Matrix-Assisted Laser Desorption Ionization (MALDI) utilizes a focused laser beam to irradiate the target sample that is co-crystalized with a matrix compound on a conductive sample plate. The ionized molecules are usually detected by a time of flight (TOF) mass spectrometer, due to their shared characteristics as pulsed techniques.

MALDI/TOF is commonly used to detect 2DE separated intact proteins because of its excellent speed, high sensitivity, wide mass range, high resolution, and contaminant-forgivingness. MALDI/TOF with capabilities of delay extraction and reflecting ion optics can achieve impressive mass accuracy at 1-10 ppm and mass resolution with m/$\Delta$m at 10000-15000 for the accurate analysis of peptides. However, the lack of MS/MS capability in MALDI/TOF is one of the major limitations for its use in proteomics applications. Post Source Decay (PSD) in MALDI/TOF does generate sequence-like MS/MS information for peptides, but the operation of PSD often is not as robust as that of a triple quadrupole or an ion trap mass spectrometer. Furthermore, PSD data acquisition and analysis is at times difficult to automate as the fragmentation can be peptide or even sequence dependent.

A newly developed MALDI TOF/TOF system (T. Rejtar et al., J. Proteomr. Res. 1(2) 171-179 (2002)) delivers many attractive features. The system consists of two TOFs and a collision cell, which is similar to the configuration of a tandem quadrupole system. The first TOF is used to select precursor ions that undergo collisional induced dissociation (CID) in the cell to generate fragment ions. Subsequently, the fragment ions are detected by the second TOF. One of the attractive features is that TOF/TOF is able to perform as many data dependent MS/MS experiments as necessary, while a typical LC/MS/MS system selects only a few abundant ions for the experiments. This unique development makes it possible for TOF/TOF to perform industry scale proteomic analysis. The proposed solution is to collect fractions from 2D LC experiments and spot the fractions onto an MALDI plate for MS/MS. As a result, more MS/MS spectra can be acquired for more reliable protein identification by database search as the quality of MS/MS spectra generated by high-energy CID in TOF/TOF is far better than PSD spectra.

It is well recognized that Fourier-Transform Ion-Cyclotron Resonance MS (FTICR-MS or more generally FTMS) is a powerful technique that can deliver high sensitivity, high mass resolution, wide mass range, and high mass accuracy. Recently, FTICR-MS coupled with LC showed impressive capabilities for proteomic analysis through Accurate Mass Tags (AMT) (Smith, R. D et al.; Proteomics. 2, 513-523, (2002)). AMT is such an accurate m/z value of a peptide that can be used to exclusively identify a protein. It has been demonstrated that, using the AMT approach, a single LC/FTICR-MS analysis can potentially identify more than $10^5$ proteins with mass accuracy of better than 1 ppm. Nonetheless, ATM alone may not be sufficient to pinpoint amino acid residue specific post-translational modifications of peptides. In addition, the instrument is prohibitively expensive at a typical cost of $650,000 or more with high maintenance requirements.

Thus, the past 100 years have witnessed tremendous strides made on the MS instrumentation with many different types of instruments designed and built for high throughput, high resolution, and high sensitivity work. The instrumentation has been developed to a stage where single ion detection can be routinely accomplished on most commercial MS systems with unit mass resolution allowing for the observation of ion fragments coming from different isotopes. In stark contrast to the sophistication in hardware, very little has been done to systematically and effectively analyze the massive amount of MS data generated by modern MS instrumentation.

In a typical mass spectrometer, the user is usually supplied with a standard material having several known ions covering the mass spectral m/z range of interest. Subject to baseline effects, isotope interferences, mass resolution, and resolution dependence on m/z, peak positions of these standard ions are determined either in terms of centroids or peak maxima through a low order polynomial fit at the peak top. These peak positions are then fit to the known peak positions through either $1^{st}$ or other higher order polynomial fit to calibrate the mass (m/z) axis.

After the mass axis calibration, a typical mass spectral data trace would then be subjected to peak analysis where peaks (ions) are identified. This peak detection routine is a highly empirical and compounded process where peak shoulders, noise in data trace, baselines due to chemical backgrounds or contamination, isotope peak interferences, etc., are considered.

For the peaks identified, a process called centroiding is typically applied to attempt to calculate the integrated peak areas and peak positions. Due to the many interfering factors outlined above and the intrinsic difficulties in determining peak areas in the presence of other peaks and/or baselines, this is a process plagued by many adjustable parameters that can make an isotope peak appear or disappear with no objective measures of the centroiding quality.

Thus, the current approaches have several pronounced disadvantages. These include:

Lack of Mass Accuracy. The mass calibration currently in use usually does not provide better than 0.1 amu (m/z unit) in mass determination accuracy on a conventional MS system with unit mass resolution (ability to visualize the presence or absence of a significant isotope peak). In order to achieve higher mass accuracy and reduce ambiguity in molecular fingerprinting such as peptide mapping for protein identification, one has to switch to an MS system with higher resolution such as quadrupole TOF (qTOF) or FTMS which come at significantly higher cost.

Large Peak Integration Error. Due to the contribution of mass spectral peak shape, its variability, the isotope peaks, the baseline and other background signals, and random noise, current peak area integration has large errors (both systematic and random errors) for either strong or weak mass spectral peaks.

Difficulties with Isotope Peaks. The current approach does not provide a good way to separate the contributions from various isotopes which usually have partially overlapped mass spectral peaks on conventional MS systems with unit mass resolution. The empirical approaches used either ignore the contributions from neighboring isotope peaks or overestimate them, resulting in errors for dominating isotope peaks and large biases for weak isotope peaks or even complete ignorance of the weaker peaks. When ions of multiple charges are concerned, the situation becomes even worse, due to the now reduced separation in mass unit between neighboring isotope peaks.

Nonlinear Operation. The current approaches use a multistage disjointed process with many empirically adjustable parameters during each stage. Systematic errors (biases) are generated at each stage and propagated down to the later stages in an uncontrolled, unpredictable, and nonlinear manner, making it impossible for the algorithms to report meaningful statistics as measures of data processing quality and reliability.

Dominating Systematic Errors. In most of MS applications, ranging from industrial process control and environmental monitoring to protein identification or biomarker discovery, instrument sensitivity or detection limit has always been a focus and great efforts have been made in many instrument systems to minimize measurement error or noise contribution in the signal. Unfortunately, the peak processing approaches currently in use create a source of systematic error even larger than the random noise in the raw data, thus becoming the limiting factor in instrument sensitivity or reliability.

Mathematical and Statistical Inconsistency. The many empirical approaches used currently make the entire mass spectral peak processing inconsistent, either mathematically or statistically. The peak processing results can change dramatically on slightly different data without any random noise or on the same synthetic data with slightly different noise. In order words, the results of peak processing are not robust and can be unstable depending on the particular experiment or data collection.

Instrument-To-Instrument Variations. It has usually been difficult to directly compare raw mass spectral data from different MS instruments due to variations in the mechanical, electromagnetic, or environmental tolerances. The current ad hoc peak processing applied on the raw data, only adds to the difficulty of quantitatively comparing results from different MS instruments. On the other hand, there is an increasing need for comparing either raw mass spectral data directly or peak processing results from different instruments or different types of instruments, for the purpose of impurity detection or protein identification through searches in established MS libraries.

In nearly all applications of mass spectrometry, it is the form of centroid mass spectral data that will be compared with known mass spectral centroid data, acquired separately, from a known database, or from theoretical isotope calculations, for the purpose of ion or ion fragment identification. When one form of acquired centroid data is compared with another form acquired earlier or on a different instrument, the above mentioned errors associated with mass determination and peak area integration (centroiding) appear twice (once for each instrument) before the actual comparison. Even when the acquired centroid data are compared to theoretically calculated accurate centroids, the actual comparison will have to be performed with a large enough tolerance (e.g., mass binning and/or de-isotoping within a nominal mass window) to reflect the large centroiding errors, especially on a lower resolution instrument such as a unit mass resolution system. The larger tolerance will undoubtedly degrade the quality of comparison/search (confidence level) and significantly slow down the computation due to the many more hits that must be evaluated (computational performance).

In many applications of mass spectrometry, such as with the use of MS/MS, electron impact (EI) ionization, electrospray ionization (ESI), and post source decay (PSD), an ion in the sample can typically be observed at multiple m/z (or mass) positions due to the creation of many fragment ions or the same ion with different charge states, or both. Even with the poorly processed centroid data mentioned above, the added information from multiple fragments can typically reduce the number of hits during a search while increasing the search confidence. This has made possible some important applications of mass spectrometry:

Compound identification based on actual GC/MS data and EI fragmentation database, e.g., a widely used library available from the National Institute of Standards and Technology (NIST) as described by S. E. Stein, J. Am. Soc. Mass Spectrom. 1999, 10, 770.

Native protein identification through multiple charge deconvolution using ESI as disclosed in the U.S. Pat. Nos. 5,300,771 and 6,118,120.

Protein or peptide database search with MS/MS data using, for example, Sequest algorithm disclosed in the U.S. Pat. No. 5,538,897.

de novo protein or peptide sequencing with MS/MS data to determine the amino acid sequences of a protein or peptide without requiring a protein or peptide database, for example, as described by A. L. Yergey, in J. Am. Soc. Mass. Spectrom. 2002, 13, 784.

Unfortunately, while adding much needed identification information, the various fragment ions observed typically have vastly varying abundances, and some fragments may not even be observable. The varying abundances of fragment ions pose some unique challenges to the above mentioned and currently widely used "centroiding first and searching or comparison second" approach. The centroiding typically has large peak integration errors associated with it, an issue further compounded by the experimentally varying abundances. This typically leads to algorithms that ignore the peak area or signal intensities through some form of normalization, for example, as disclosed in the U.S. Pat. No. 5,538,897. While normalization provides an easy solution computationally, it inevitably results in the loss of valuable information regarding the likelihood of a particular ion fragment under consideration. Given that ion counting noise is the typical dominating source of noise in ion or fragment detection, a higher intensity or signal level directly translates to a higher probability for the presence of the particular ion fragment. To make the matter worse, all intensity normalization schemes destroy the intrinsic statistical relationship between the ion and its multiple fragments, making it difficult (if not impossible) to statistically assess the presence or absence of an ion under consideration. As a result, heuristic assessment is used through the "training" of the search algorithm on hundreds or thousands of "typical" mass spectra, when in fact all statistical measures can be derived directly from the acquired mass spectrum itself.

Thus, there exists a significant gap between what the current mass spectral instrumentation can offer and what is being achieved at the present using existing technologies for mass spectral analysis.

SUMMARY OF THE INVENTION

It is an object of the invention to provide a mass spectrometry system and a method for operating a mass spectrometry system that overcomes the disadvantages described above, in accordance with the methods described herein.

It is another object of the invention to provide a storage media having thereon computer readable program code for causing a mass spectrometry system to perform the method in accordance with the invention.

It is a further object of the invention to provide mass spectrometry libraries that are richer in information, and more accurate than current stick spectra libraries.

An additional aspect of the invention is, in general, a computer readable medium having thereon computer readable code for use with a mass spectrometer system having a data analysis portion including a computer, the computer readable code being for causing the computer to analyze data by performing the methods described herein. The computer readable medium preferably further comprises computer readable code for causing the computer to perform at least one the specific methods described.

Of particular significance, the invention is also directed generally to a mass spectrometer system for analyzing chemical composition, the system including a mass spectrometer portion, and a data analysis system, the data analysis system operating by obtaining calibrated continuum spectral data by processing raw spectral data; generally in accordance with the methods described herein. The data analysis portion may be configured to operate in accordance with the specifics of these methods. Preferably the mass spectrometer system further comprises a sample preparation portion for preparing samples to be analyzed, and a sample separation portion for performing an initial separation of samples to be analyzed. The separation portion may comprise at least one of an electrophoresis apparatus, a chemical affinity chip, or a chromatograph for separating the sample into various components.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENTS

Figure 1:
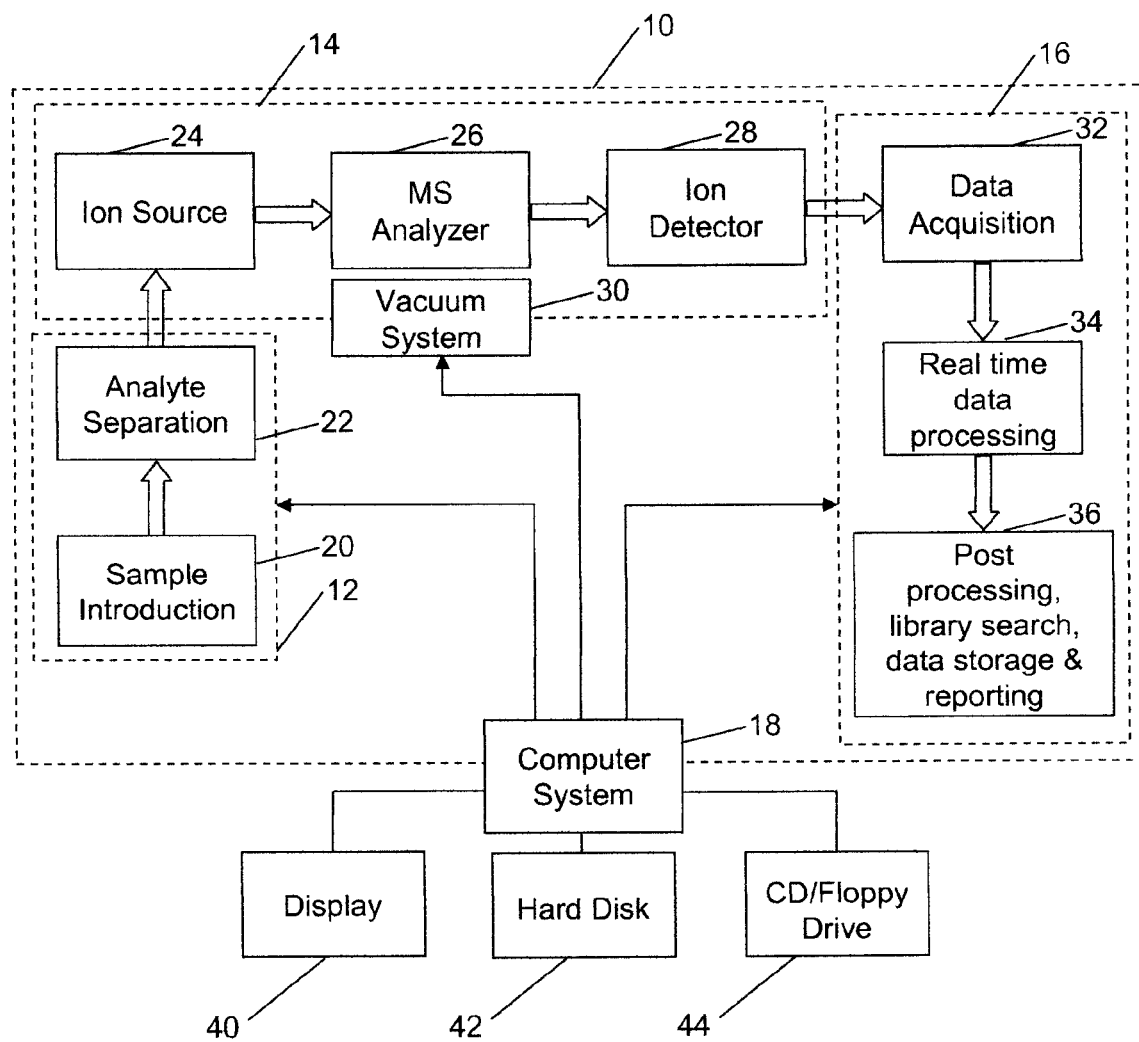
FIG. 1 is a block diagram of a mass spectrometer in accordance with the invention.

Referring to FIG. 1, there is shown a block diagram of an analysis system 10, that may be used to analyze proteins or other molecules, as noted above, incorporating features of the present invention. Although the present invention will be described with reference to the single embodiment shown in the drawings, it should be understood that the present invention can be embodied in many alternate forms of embodiments. In addition, any suitable types of components could be used.

Analysis system 10 has a sample preparation portion 12, a mass spectrometer portion 14, a data analysis system 16, and a computer system 18. The sample preparation portion 12 may include a sample introduction unit 20, of the type that introduces a sample containing proteins or peptides of interest to system 10, such as Finnegan LCQ Deca XP Max, manufactured by Thermo Electron Corporation of Waltham, Mass., USA. The sample preparation portion 12 may also include an analyte separation unit 22, which is used to perform a preliminary separation of analytes, such as the proteins to be analyzed by system 10. Analyte separation unit 22 may be any one of a chromatography column, an electrophoresis separation unit, such as a gel-based separation unit manufactured by Bio-Rad Laboratories, Inc. of Hercules, Calif., and is well known in the art. In general, a voltage is applied to the unit to cause the proteins to be separated as a function of one or more variables, such as migration speed through a capillary tube, isoelectric focusing point (Hannesh, S. M., *Electrophoresis* 21, 1202-1209 (2000), or by mass (one dimensional separation)) or by more than one of these variables such as by isoelectric focusing and by mass. An example of the latter is known as two dimensional electrophoresis.

The mass spectrometer portion 14 may be a conventional mass spectrometer and may be any one available, but is preferably one of MALDI-TOF, quadrupole MS, ion trap MS, qTOF, TOF/TOF, or FTMS. If it has a MALDI or electrospray ionization ion source, such ion source may also provide for sample input to the mass spectrometer portion 14. In general, mass spectrometer portion 14 may include an ion source 24, a mass analyzer 26 for separating ions generated by ion source 24 by mass to charge ratio, an ion detector portion 28 for detecting the ions from mass analyzer 26, and a vacuum system 30 for maintaining a sufficient vacuum for mass spectrometer portion 14 to operate efficiently. If mass spectrometer portion 14 is an ion mobility spectrometer, generally no vacuum system is needed and the data generated are typically called a plasmagram instead of a mass spectrum.

The data analysis system 16 includes a data acquisition portion 32, which may include one or a series of analog to digital converters (not shown) for converting signals from ion detector portion 28 into digital data. This digital data is provided to a real time data processing portion 34, which process the digital data through operations such as summing and/or averaging. A post processing portion 36 may be used to do additional processing of the data from real time data processing portion 34, including library searches, data storage and data reporting.

Computer system 18 provides control of sample preparation portion 12, mass spectrometer portion 14, and data analysis system 16, in the manner described below. Computer system 18 may have a conventional computer monitor 40 to allow for the entry of data on appropriate screen displays, and for the display of the results of the analyses performed. Computer system 18 may be based on any appropriate personal computer, operating for example with a Windows® or UNIX® operating system, or any other appropriate operating system. Computer system 18 will typically have a hard drive 42, on which the operating system and the program for performing the data analysis described below is stored. A drive 44 for accepting a CD or floppy disk is used to load the program in accordance with the invention on to computer system 18. The program for controlling sample preparation portion 12 and mass spectrometer portion 14 will typically be downloaded as firmware for these portions of system 10. Data analysis system 16 may be a program written to implement the processing steps discussed below, in any of several programming languages such as C++, JAVA or Visual Basic.

For a given mass spectrum, the following basic model can be constructed:

$$r=Kc+e \quad \text{Equation 1}$$

where r is an (n×1) matrix of the profile mode mass spectral data measured of the sample, digitized at n m/z values; c is a (p×1) matrix of regression coefficients which are representative of the concentrations of p ions or fragments in the sample; K is an (n×p) matrix composed of profile mode mass spectral responses for the p components, all sampled at the same n m/z points as r; and e is an (n×1) matrix of a fitting residual with contributions from random noise and any systematic deviations from this model.

The components arranged in the columns of matrix K will be referred to as peak components, which may optionally include any baseline of known functionality such as a column of 1's for a flat baseline or an arithmetic series for a sloping baseline. A key peak component in matrix K is the known mass spectral response for the ion or fragment of interest, which can either be experimentally measured or theoretically calculated.

When the ion or fragment of interest has been identified with its elemental composition known, it is preferred that the peak component in matrix K be calculated as the convolution of the theoretical isotope distribution and the known mass spectral peak shape function. This known mass spectral peak shape function may be directly measured from a section of the mass spectral data, mathematically calculated from actual measurements through deconvolution, or given by the target peak shape function if a comprehensive mass spectral calibration has already been applied, all using the approach outlined in U.S. Pat. No. 6,983,213 and International Patent Application PCT/US2004/034618 filed on Oct. 20, 2004.

When the ion or fragment of interest has not been identified (has an unknown elemental composition), actual measured profile mode MS data may be used as a peak component in K. This actual measured profile mode MS data can be from, for example, an established library of many ions or fragments, which may have been measured on a different instrument (or instruments) of preferably higher resolution and quality. It is preferred that these library mass spectra have been calibration using the above mentioned comprehensive mass spectral calibration process involving peak shape functions to insure as close a match as possible between r and K in terms of mass spectral peak shape functions. Alternatively, the centroid data from a library, such as the EI library from NIST as described by S. E. Stein, J. Am. Soc. Mass Spectrom. 1999, 10, 770, can be convoluted with a peak shape function matching that for the spectrum in r to create peak components for inclusion in K.

It should be noted that there is no need to perform any baseline correction on the actual measured mass spectral data in r or K as any difference in baseline between a peak component in K and the sample measurement in r will be fully compensated for by the baseline components also included in K.

It should also be noted that a peak component included in K does not have to correspond to a pure ion or fragment. It can be a linear combination of a few ions or fragments, as would be the case when isotope labeled protein or peptide fragments are involved in MS/MS experiment. In this case, the isotope pattern for each ion or fragment can be calculated or measured separately before combining the isotope patterns with given concentration ratios to form a single peak component in K.

Optionally, one or more first derivatives corresponding to that of a peak component, a known linear combination of several peak components, or the measured mass spectral data r may be added into the peak components matrix K to account for any relative mass spectral errors between r and K.

Once proper peak components matrices are arranged into the matrix K, including any known interfering ions and labeled isotopes if applicable, the model above can be solved for concentration vector c for a given mass spectral response r, in a regression process, $$c=K^+r \quad \text{Equation 2}$$

where $K^+$ is a form of the inverse of K, which can, for example, take the form of:

$$K^+=(K^TK)^{-1}K^T$$

as a least squares solution, which is described by John Neter et al., in *Applied Linear Regression*, $2^{nd}$ Ed., Irwin, 1989, p. 206, the entire disclosure of which is incorporated by reference herein.

The concentration vector c contains the concentration information of all included peak components including any baseline contribution automatically determined. For derivatives included, the corresponding coefficients in concentration vector c contain the relative mass error information for the given components included in the peak component matrix.

For most mass spectrometry applications where the noise in the mass spectral response r typically comes from ion shot noise, it is advantageous to use weighted regression in the above model where the weight at each mass sampling point would be inversely proportional to the signal variance at this mass spectral sampling point, i.e., the mass spectral intensity in r. This is further described by John Neter et al., in *Applied Linear Regression*, $2^{nd}$ Ed., Irwin, 1989, p. 418, the entire disclosure of which is incorporated by reference herein.

In addition to the estimated c from Equation 2, which contains quantitative information critical for quantitative analysis, there is other equally important qualitative information that can be derived from the mass spectral data r through the same regression analysis, such as the statistical significance level for each peak component in K through a t-statistic measure, $$t^* = c_i/s_i \qquad \text{Equation 3}$$

where $s_i$ is the standard deviation estimate for a particular peak component i in its concentration estimate $c_i$, all using the approach outlined in U.S. Pat. No. 6,983,213 and International Patent Application PCT/US2004/034618 filed on Oct. 20, 2004.

For this t-statistic, a p-value can be defined as the probability that a non-existing ion with expected concentration of zero could have generated a high enough signal with the t value given in Equation 3, or, $$p[t(df) > t^*] \qquad \text{Equation 4}$$

i.e., the false positive probability for this ion or fragment. In Equation 4, t(df) is the t distribution of the concentration estimate at given degrees of freedom df. Typically, the higher the t-statistic in Equation 3, the smaller the p-value, and the more likely this ion or fragment exists. The t-distribution, p-value and degrees of freedom df are all described by John Neter et al., in *Applied Linear Regression*, $2^{nd}$ Ed., Irwin, 1989, p. 8, p. 12, and p. 7, the entire disclosure of which is incorporated by reference herein.

When the ion or fragment signal is not very high, especially at low level ion abundances, the p-value from Equation 4 may not be small enough to give enough statistical confidence related to the likely presence of the given ion or fragment. Fortunately for many MS applications, there are multiple observations available for the same ion, due either to ion fragmentations in the ion source such as EI, tandem MS/MS experiments, post source decay (PSD) or other decays or ion reactions inside a mass analyzer such as dehydration or sodium adduct formation. In electrospray ionization (ESI) of large bio-molecules such as proteins or peptides, the same ion can be charged with multiple charge states all in the same experiment, creating multiple observable signals at various m/z values or masses.

While the above model, its solution, and the associated statistics can be easily adapted to include the whole mass spectral range with multiple observable ions or fragments, it will suffer from the varying ionization or fragmentation efficiencies among the different fragments, as pointed out in international patent application PCT/US2004/013096, filed on Apr. 28, 2004. A preferred approach would be to apply the above approach from Equation 1 to 4 in a limited mass spectral range on a per-fragment or per-ion basis, to effectively avoid the issue of varying ionization/fragmentation efficiencies and arrive at a p-value for each fragment or ion j, $p_j$. Each p-value $p_j$ represents the false positive probability for the corresponding j-th ion or fragment resulting from the same starting ion. While $p_j$ could vary widely from one ion or fragment to another, depending on its abundance and the noise in its measurement, an overall false positive statistic can be established based on the individual $p_j$'s through the following equation, $$p = p_1 \cdot p_2 \cdots p_J \qquad \text{Equation 5}$$

where J is the total number of ions or fragments observed from the same starting ion. Alternatively, the probability for the presence of the given starting ion can be calculated as $1-p$.

The benefit of measuring a starting ion through multiple ions or fragments can now be seen immediately where the overall p-value or false positive probability can be drastically reduced due to the multiplication of individual p-values. In addition, as is well known in tandem MS/MS analysis of proteins and peptides, there are many peptides that may have very different amino acid sequences with exactly the same elemental composition (and same exact mass) which will have identical MS signals, making it impossible to distinguish one from the other. For example, three peptides TIYTPGSTVLYR, SKDVFLNSVFSK, and QSDFTFGKVTIK all have identical elemental composition $C_{63}H_{100}N_{15}O_{19}^+$ with the same exact mass of 1370.7320 Da, making them indistinguishable even on high resolution FTMS systems. When analyzed in tandem MS/MS mode, however, very different fragments will be generated from these peptides with very different $p_j$ values in Equation 5, resulting in very different overall p values to clearly differentiate one from the other.

Compared to other alternatives currently in use or being proposed, this approach represents a new and fast approach to MS analysis with significant advantages:

a. Due to its sound mathematical and statistical basis, this approach eliminates the many ad hoc and nonlinear operations in current mass spectral processing and protein/peptide library searching, resulting in a theoretically elegant process for the application of general MS analysis to proteomics.

b. The analysis can be accomplished based on a single conventional MS measurement of multiple ions or fragments associated with the given ion of interest with all probability measures derived from this single MS measurement itself.

c. This approach bypasses the complicated, error-prone, and ad hoc mass spectral peak detecting processes altogether, with noise filtering and spectral smoothing automatically built-in.

d. By working with all known and significant isotopes from databases or actual measured mass spectral profiles without centroiding errors, complete data integrity is preserved with all isotope patterns automatically included in the analysis or search.

e. The one ion or fragment at a time approach in this invention not only avoids the problem of varying ion or fragment abundances, but also derives individual probability measures which can then be combined into an overall probability measure for the starting ion of interest.

f. Instead of ad hoc scoring, statistically rigorous confidence level such as t-statistics or p-values can be established for a given ion to test for its presence or absence in the sample and used to rank possible candidates for compound identification including protein/peptide identification or database search.

Thus, this approach provides an easy, fast, yet mathematically sound and statistically rigorous measure for general compound identification through the use of multiple ions or fragments with applications to either de novo protein or peptide sequencing or database search.

Figure 2:
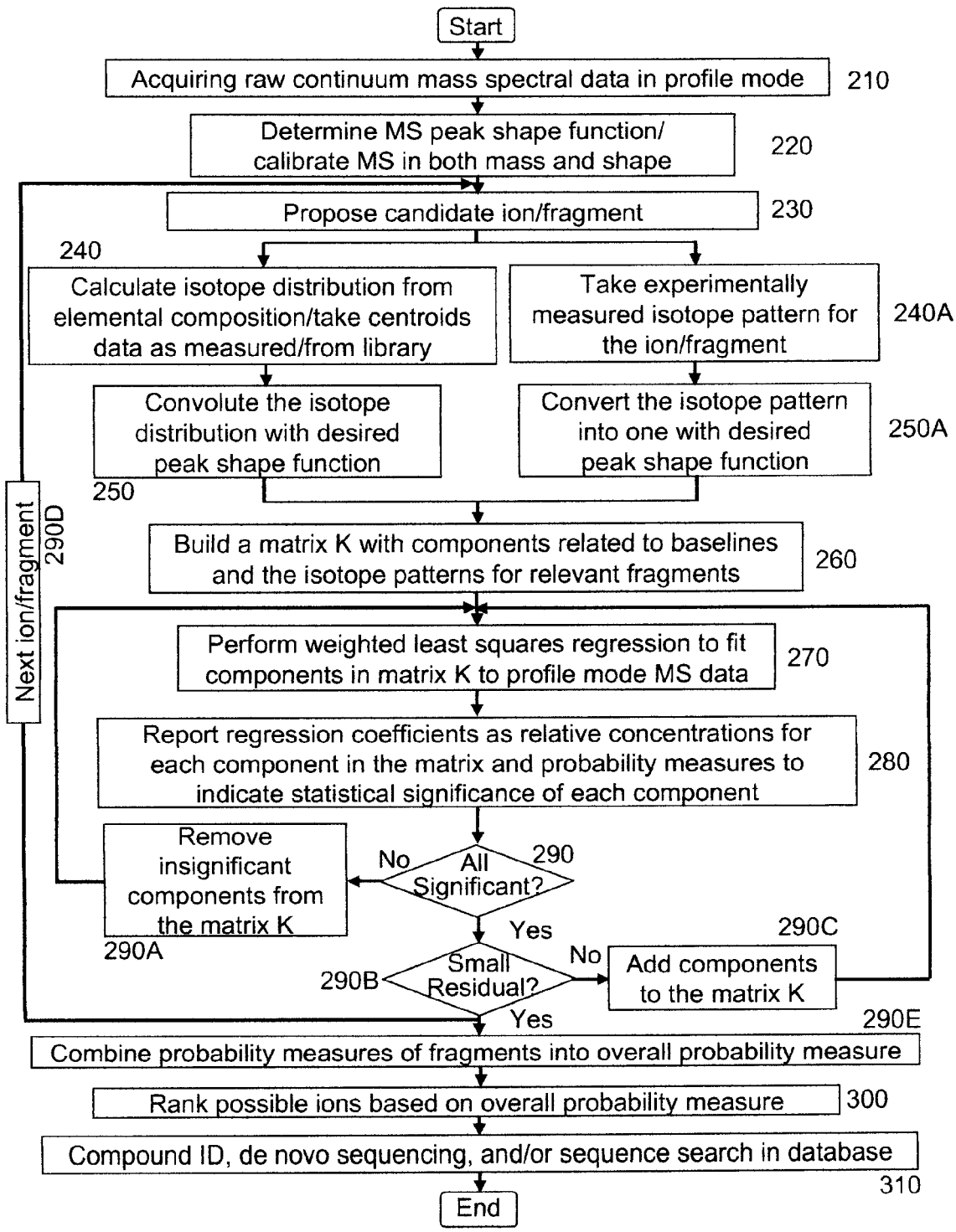
FIG. 2 is flow chart of the steps in the analysis used by the system of FIG. 1.

Referring to FIG. 2, at step 210, raw continuum mass spectral data is obtained for a sample containing, for example, tandem MS/MS spectrum containing many isotope patterns or clusters corresponding to the many fragments of a given peptide. While, as mentioned above, most commercial techniques utilize stick spectral data, it will be recognized that the use of the entire raw spectrum means that data is not lost due to a premature gross simplification of the features of the data. However, this raw spectrum has characteristics relating to instrument peak shape function, instrument resolution, and baseline variations due to spurious ions and neutral particles that may reach the detector. Further, there may be a mass dependence with respect to all of these potential factors. For example, there is an exponential decay of baseline displacement as a function of increasing m/z in a MALDI system, principally due to ions of the matrix material, some of which arrive at the detector, despite every attempt to reduce their presence.

At step 220, the raw data acquired in step 210 is subjected to a full calibration of the mass spectrometer based on internal and/or external standards so as to standardize the raw continuum data. This assures that the peaks are lined up at the proper m/z values, and that the shape of the peaks is properly defined and known mathematically. This is preferably accomplished by the procedure set forth in U.S. Pat. No. 6,983,213 and International Patent Application PCT/US2004/034618 filed on Oct. 20, 2004, the entire contents of which are incorporated herein by reference. Instead of a full mass spectral calibration, the peak shape function can be calculated and used in the following mass spectral search process, at the expense of reduced mass accuracy during the search.

At step 230, candidate ion fragments are selected and proposed for matching with one observed isotope pattern or cluster in the mass spectrum. There are several approaches that can be used to select a candidate ion or fragment at this stage:

a. For an MS/MS search of peptides/proteins in the absence of any database, the multiple fragments within an MS/MS spectrum provides important information to deduce the amino acid sequences for the peptide of interest, i.e., de novo sequencing. One could start at one end of the mass spectrum and optionally measure the accurate monoisotopic mass of a first or last isotope cluster. This first or last isotope cluster would typically correspond to one of the 20 known amino acids. Occasionally due to incomplete fragmentation, these two isotope clusters may correspond to two amino acids drawn from a pool of 20 known amino acids, with replacement. In other cases these two isotope clusters may contain one or a few amino acids with some modifications such as oxidation (addition of O or $O_2$ to methionine), dehydration (loss of $H_2O$), phosphorylation (addition of $HPO_3$ on tyrosine, serine, and threonine), sulphation (on the O of tyrosine), and glycosylation. In any case, a candidate fragment can be selected computationally efficiently with or without accurate monoisotopic mass measurement as a pre-filter through the elemental composition search disclosed in international patent application PCT/US2005/039186, filed on Oct. 28, 2005. One may select more than one candidate fragment to start and either drop some obviously incorrect ones later on while more fragments are processed, or keep them all until the analysis is complete to select the winner, at step 300. After completing the analysis of the current isotope cluster, one would move on to the next isotope cluster by proposing a new fragment to match the measured isotope cluster. This new fragment can be formed by adding to or deleting from the previous fragment, a new segment. This new segment is typically composed of one or a few of the 20 known amino acids including possible complications such as modifications and incomplete fragmentations. The same elemental composition search would be used to select and propose the new fragment(s). Other modifications such as isotope tags or enzymatic modifications on terminus can also be incorporated. Similar approaches can be applied to other more general or specific polymers including DNA molecules composed of A, G, T, and C bases in a chain.

b. For an MS/MS search of peptides/proteins through a database, the same approach as described above for de novo sequencing can be used to select and propose fragments, except that not every one of the 20 amino acids would be possible at each stage due to the limited known sequences available in the protein or peptide databases after in sillico digestion with known enzymes. Further reduction in the search space can be achieved through accurate mass measurement on the peptide that generates the MS/MS fragments, i.e., the precursor ion, thus limiting the search to only those peptides that have exact masses within a tight, accurate mass window. Searching with known sequences and possible modifications also becomes easier as some modifications are specific to amino acids or sequences and can be eliminated based on the known sequences. Other modifications such as isotope tags or enzymatic modifications on terminus can obviously be incorporated. Similar approaches can be applied to other more general or specific polymers for search in a known library, e.g., DNA molecules composed of A, G, T, and C bases in a chain given by a genomics library.

c. For the multiplying charged proteins or peptides from ESI experiment in the presence of a protein or peptide database, the charge state of each observed ion in the series needs to be determined and used to calculate the intact protein or peptide's mass, for example, as disclosed in U.S. Pat. Nos. 5,300,771 and 6,118,120. The calculated protein or peptide mass can then be used to generate a list of possible proteins or peptides from the database. Each of these possible proteins/peptides associated with a given charge can now be selected as a candidate ion whereas the same protein/peptide with a different charge will be selected as the next candidate ion.

d. For in source fragmentation such as EI fragmentation in, for example, GC/MS applications, or PSD, or other types of fragmentations inside a mass spectrometry system, it would be ideal to have all observed fragments elucidated in terms of elemental compositions, so that each of these fragments along with its elemental compositions can be used as candidate fragments. This, however, may not always be possible, as is the case with the NIST EI mass spectral library, where all EI fragments of over 100,000 compounds have been experimentally measured in centroid mode, but not elucidated in terms of elemental compositions.

e. When there are experimental fragmentation data available in centroid mode such as the NIST EI library, one can take each fragment's centroid data as the candidate fragment for the next stage processing. It is appreciated however that centroid data with all available isotopes would be preferred to maintain the data integrity. In the NIST EI library, relative intensity data are also available for various fragments of a compound, and has been used in the currently available searching algorithms. In order for this search to work properly, however, the MS instrument must be painstakingly tuned to insure peak ratios within 20-30% error bounds of expected values, for example, as mandated by the QC procedure of United States Environmental Protection Agency (USEPA) Method 525.2 with the use of decafluorotriphenylphosphine (DFTPP) as the tuning compound.

For those skilled in the art, it is well known that fragment abundance ratios change as much from one compound to another as with instrument conditions and therefore are very difficult to maintain even on a well tuned instrument. It is appreciated that, in this invention, the relative intensities of fragments in a library are no longer relevant, and the actual measured fragment intensity will be used to assess the probability of a given fragment before the establishment of an overall probability based on all of the fragments.

f. When there are experimental fragmentation data available in continuum mode, better data integrity and performance can be expected, especially if the experimental data have been collected on a mass spectrometer with a resolution higher than the one used in step 210 and/or a full mass spectral calibration is available on the experimental fragmentation data, using preferably the approach outlined in U.S. Pat. No. 6,983,213 and International Patent Application PCT/US2004/034618 filed on Oct. 20, 2004. In this case, the experimentally measured isotope pattern, or pattern for each observed fragment, can be used as a candidate fragment after a convolution or calibration step, to have the observed isotope pattern conform to a desired peak shape function.

g. When the experimentally measured fragmentation data come from a high mass accuracy instrument such as qTOF or even FTMS, or a unit mass resolution system with comprehensive mass spectral calibration as outlined in U.S. Pat. No. 6,983,213 and International Patent Application PCT/US2004/034618 filed on Oct. 20, 2004, an elemental composition determination can be carried out for each observed fragment, using either commercially available formula search algorithms or preferably the approach outlined in international patent application PCT/US2005/039186, filed on Oct. 28, 2005.

At step 240, the exact mass locations for the candidate ion/fragment is calculated based on its elemental composition if available. This includes theoretically calculated isotope distributions, which are taken into account in the manner described in U.S. Pat. No. 6,983,213 and International Patent Application PCT/US2004/034618 filed on Oct. 20, 2004. Alternatively, one can use the centroid data, experimentally measured and/or from a library, as the isotope distributions.

At step 250 the isotope distribution is convoluted with the peak shape function calculated or specified as the target peak shape function in the full mass spectral calibration, all given in step 220, to obtain a calculated isotope pattern (mass spectral continuum) for the candidate ion/fragment. As used herein, for this purpose, and for other purposes throughout this document, the term convolution may refer to matrix operations, or point by point operation in Fourier transform space, or any other type of convolution, filtering, or correlation, either of a traditional type, or not.

As an alternative to steps 240 and 250, steps 240A and 250A take an isotope pattern in profile or continuum mode as measured from an instrument or from a library and convert the isotope pattern to have desired peak shape function consistent with what is calculated (actual peak shape function) or transformed into (target peak shape function) in step 220. This is achieved by either a separate full mass spectral calibration, just as the one in step 220, performed on this isotope pattern, or through a convolution of the isotope pattern measured on a higher resolution system here with the peak shape function from step 220. When the isotope pattern is measured with high resolution, the original peak shape function observed in it becomes insignificant compared to the peak shape function in step 220.

At step 260, a matrix K is generated to include known and sometime mass-dependent baseline functions and the isotope pattern for the candidate ion/fragments. Examples of possible baseline functions include a flat line and several lower order terms such as linear or quadratic terms. The combination of these lower order terms can adequately compensate for an exponentially decaying baseline within a small mass spectral range, and help arrive at the computationally efficient linear solutions in step 270, though one may choose to incorporate the nonlinear terms explicitly and seek a nonlinear solution instead. Matrix K may optionally contain any other components interfering with the candidate fragment's isotope pattern such as the isotope patterns from co-existing ions or fragments including isotope labeled version of the fragments. To model the possible mass offset between r and components in K, the first derivatives of the components in K or the first derivative of the sample measurement r may also be included.

At step 270, a classical least squares regression (or weighted least squares regression with all weights equal to one) is performed to fit the components of the matrix generated in step 260 to the acquired and/or calibrated mass spectral spectrum data of step 220, in the form given in Equations 1-2.

At step 280, the regression coefficients (values in c) are reported out as the relative concentrations for components included in matrix K along with probability measures in the form of either t-statistic or p-value as given in Equations 3-4.

At step 290 a statistical test based on t-statistic, p-value, or other measures such as F-statistic is performed to determine whether any or all of components included in the matrix K are significant. In this regard, the baseline may be treated in the analysis as if it is another compound found in the sample (in the data produced in step 220). If any component is insignificant, then branching to step 290A occurs, and this component is removed from the matrix K before the next iteration back to step 270 (and continuing on to steps 280 and 290). This process of first estimating the contribution of the possible components as part of an overall fit, followed by the removal of insignificant baseline components serves the purpose of unbiased correction of components including baselines without unnecessarily introducing extra components into matrix K and Equation 1. Typically as more components are added to the matrix K, its conditioning would get worse, resulting in less precise estimation of concentrations and a worsening of other statistical confidence. However, by removing all insignificant components in the process, the conditioning of the K matrix is improved, leading to more precise concentration estimates for c and higher statistical confidence. This iterative removal of some components at this points optional.

When all insignificant components have been removed, at step 290B, a statistical test on the residual e (Equation 1) is performed to check and see if there are other components missing in the matrix K resulting in larger than expected residuals, in which case more components may be added in step 290C before returning to step 270 for another iteration. These components may be an isotope labeled version of the fragment involved, or may be a fragment from an interfering precursor ion not separated in time and mass during the survey scan of an LC/MS/MS experiment.

When all components are deemed significant with statistically insignificant residuals, one would go through step 290D and return to step 230 for the analysis of the next ion/fragment. When all ions/fragments have been analyzed, the individual probability measures pertaining to each ion/fragment can be combined to form an overall probability measure for the ion that generates these fragments observed in r, in step 290E. Equation 5 above shows an example of how to progress from individual p-values to an overall p-value.

When multiple possible ions are considered along with their corresponding fragments, their overall probability measures can be used to rank these ions in step 300 and to report this as analysis or search results.

In the absence of a known library or list of possible ions, the results reported in step 300 can be used for unknown compound identification including de novo sequencing, where the amino acid sequence for a previously unknown peptide or protein can be determined. In the presence of a library such as a protein/peptide library, the possible peptides or proteins selected from the library can be sorted in a search report based on their overall probability measures as scores. Some combinations of various steps can be conceived by those skilled in the art, such as always performing an analysis as if there is no known protein or peptide library available, i.e., de novo sequencing, to determine the amino acid sequence before searching in an available library, in which case a simple and very fast text string search can be performed on the sequence through the use of known computational techniques such as BLAST.

These probability measures are reported out by computer 18 (FIG. 1) by being displayed on the monitor 40 and/or by printing on a printer (not shown) associated with computer 18.

For all the analysis described above, it may be advantageous to transform the m/z axis into another more appropriate axis before hand, to allow for analysis with a uniform peak shape function in the transformed axis, as pointed out in U.S. Pat. No. 6,983,213 and International Patent Application PCT/US2004/034618 filed on Oct. 20, 2004.

On high resolution MS systems such as qTOF or FTMS, the various isotope satellites of the same ion may be spectrally well separated from each other, may be interleaved with the isotope satellites of other ions in between, may have intensities located at a different nonlinear part of the ion detector response curve, may have different mass shifts due to space charges, and may have different baselines, etc. For these reasons, it may be advantageous to analyze the ion through individually analyzing its many satellite isotopes, as a special case of the analysis method described above, so that each isotope satellite can be treated separately before combining to complete the analysis of the ion. One satellite isotope is the monoisotope, which may be advantageously used due to its simplicity, to propose initial possible elemental compositions for later confirmation and ranking, based on all observable satellite isotopes. In this case, each addition candidate ion (satellite isotope here) would have its elemental composition derived from other candidate ion (satellite isotope also) by switching one or more isotopes in its elemental composition.

The process described above includes a fairly comprehensive series of steps, for purposes of illustration, and to be complete. However, there are many ways in which the process may be varied, including leaving out certain steps, or performing certain steps before hand or "off-line". For example, it is possible to conduct a calibration once, and to use that calibration for some period of time with the same instrument. In addition, one may less desirably omit step 220 in FIG. 2 and work with assumed peak shape functions using only a conventional multi-point mass axis calibration with rudimentary level of mass accuracy. Furthermore, the operations performed on the spectra in the library need only be performed once, and the resulting calibrated library spectra with a given target peak shape function may be used for all instruments or even instrument types that are fully calibrated to the same target peak shape function. In this regard, a calibrated library produced in accordance with the invention is a very valuable commodity that can be sold separately, because it has high intrinsic value to different users of different mass spectrometer systems that are standardized with respect to the same peak shape functions.

Conversely certain steps may be combined or performed at the same times as other steps. For example, if one or more known compounds or fragments are available as internal standards in the sample, they will generate known spectra, which may be used to perform an on-the-fly full mass spectral calibration in the manner described in the U.S. Pat. No. 6,983,213 and International Patent Application PCT/US2004/034618 filed on Oct. 20, 2004.

It will be understood that on some occasions, not all of the ions or ion fragments in a sample will be found in the library. New molecules will be discovered. If this is the case, there will be an extra component or components for which no determination of concentration can be made, at least initially, that will reduce the fitting residual e in Equation 1 down to measurement noise level, until the identity and chemical composition of the unknown species have been determined. Then either the library of stick spectra or a pre-calculated library of continuum spectra can be augmented by ions or fragments from new compounds not already included in the relevant library, for use in future analysis.

It is noted that the terms "mass" and "mass to charge ratio" are used somewhat interchangeably in connection with information or output as defined by the mass to charge ratio axis of a mass spectrometer. This is a common practice in the scientific literature and in scientific discussions, and no ambiguity will occur, when the terms are read in context, by one skilled in the art.

The methods of analysis of the present invention can be realized in hardware, software, or a combination of hardware and software. Any kind of computer system—or other apparatus adapted for carrying out the methods and/or functions described herein—is suitable. A typical combination of hardware and software could be a general purpose computer system with a computer program that, when being loaded and executed, controls the computer system, which in turn control an analysis system, such that the system carries out the methods described herein. The present invention can also be embedded in a computer program product, which comprises all the features enabling the implementation of the methods described herein, and which—when loaded in a computer system (which in turn control an analysis system), is able to carry out these methods.

Computer program means or computer program in the present context include any expression, in any language, code or notation, of a set of instructions intended to cause a system having an information processing capability to perform a particular function either directly or after conversion to another language, code or notation, and/or reproduction in a different material form.

Thus the invention includes an article of manufacture, which comprises a computer usable medium having computer readable program code means embodied therein for causing a function described above. The computer readable program code means in the article of manufacture comprises computer readable program code means for causing a computer to effect the steps of a method of this invention. Similarly, the present invention may be implemented as a computer program product comprising a computer usable medium having computer readable program code means embodied therein for causing a function described above. The computer readable program code means in the computer program product comprising computer readable program code means for causing a computer to effect one or more functions of this invention. Furthermore, the present invention may be implemented as a program storage device readable by machine, tangibly embodying a program of instructions executable by the machine to perform method steps for causing one or more functions of this invention.

It is noted that the foregoing has outlined some of the more pertinent objects and embodiments of the present invention. The concepts of this invention may be used for many applications. Thus, although the description is made for particular arrangements and methods, the intent and concept of the invention is suitable and applicable to other arrangements and applications. It will be clear to those skilled in the art that other modifications to the disclosed embodiments can be effected without departing from the spirit and scope of the invention. The described embodiments ought to be construed to be merely illustrative of some of the more prominent features and applications of the invention. Thus, it should be understood that the foregoing description is only illustrative of the invention. Various alternatives and modifications can be devised by those skilled in the art without departing from the invention. Other beneficial results can be realized by applying the disclosed invention in a different manner or modifying the invention in ways known to those familiar with the art. Thus, it should be understood that the embodiments has been provided as an example and not as a limitation. Accordingly, the present invention is intended to embrace all alternatives, modifications and variances which fall within the scope of the appended claims.

What is claimed is:

1. A method for analyzing an ion when at least two ions or fragments are present, comprising the steps of:
    obtaining the isotope pattern for at least one candidate ion or fragment;
    constructing a peak component matrix including said isotope pattern;
    obtaining measured mass spectral response;
    performing a regression between measured profile mode mass spectral response and the peak component matrix;
    reporting a probability measure for said candidate ion or fragment;
    selecting at least one candidate ion or fragment based on the probability measure as the possible matching ion or fragment;
    combining said probability measures of at least two said matching ions or fragments into an overall probability measure for an ion.

2. The method of claim 1, where the isotope pattern has the desired peak shape function.

3. The method of claim 2, where the desired peak shape function is one of assumed peak shape function, actual peak shape function as one of measured and calculated, and target peak shape function.

4. The method of claim 2, where the isotope pattern is measured in profile mode.

5. The method of claim 4, where the measurement is performed at a higher MS resolution.

6. The method of claim 4, where the measured isotope pattern has been converted to have a desired peak shape function.

7. The method of claim 6, where a desired peak shape function is one of assumed peak shape function, actual peak shape function as one of measured and calculated, and target peak shape function from a mass spectral calibration involving peak shape.

8. The method of claim 2, where the isotope pattern is a linear combination of at least two ions or fragments.

9. The method of claim 8, where the at least two ions or fragments include native and isotope labeled versions of the ion or fragment.

10. The method of claim 1, where the measured mass spectral response has been calibrated to have a desired peak shape function.

11. The method of claim 10, where a desired peak shape function is one of assumed peak shape function, actual peak shape function as one of measured and calculated, and target peak shape function from a mass spectral calibration involving peak shape.

12. The method of claim 1, where the isotope pattern is theoretically calculated through the convolution of isotope distribution and a desired peak shape function.

13. The method of claim 12, where a desired peak shape function is one of assumed peak shape function, actual peak shape function as one of measured and calculated, and target peak shape function from a mass spectral calibration involving peak shape.

14. The method of claim 12, where the isotope distribution is theoretically calculated from at least one elemental composition.

15. The method of claim 12, where an elemental composition is obtained through a search of possible elemental compositions using the measured mass spectral response.

16. The method of claim 12, where the isotope distribution is representative of an actual MS measurement in centroid mode.

17. The method of claim 12, where the isotope distribution is determined with reference to a known library of previously measured or calculated centroid MS data.

18. The method of claim 1, where the at least two ions or fragments are generated from including one of tandem mass spectrometry, in-source fragmentation, post source decay, ion reaction inside a mass analyzer including an ion trap, electron impact ionization, and electrospray ionization.

19. The method of claim 1, where said ions or fragments are derived from at least one of peptides or proteins.

20. The method of claim 1, where said ions or fragments are derived from a combination of ions produced from the original ion, including the intact ion, the adduct ion formed with sodium, and the modified ion after dedydration.

21. The method of claim 1, where said ions or fragments are derived from a part of a polymer.

22. The method of claim 21 where the polymer is from a DNA molecule.

23. The method of claim 1, where the peak component matrix contains baseline components which are at least one of linear and nonlinear in nature.

24. The method of claim 1, where the peak component matrix contains first derivative of at least one of the measured mass spectral response and an isotope pattern already included in the peak component matrix.

25. The method of claim 1, where the peak component matrix contains at least one of the isotope pattern and its first derivative of any interfering ions.

26. The method of claim 1, where the regression is a multiple linear regression.

27. The method of claim 1, where the regression is a weighted regression.

28. The method of claim 27, where the weights are all ones.

29. The method of claim 27, where the weights are inversely proportional to the mass spectral variance.

30. The method of claim 29, where the mass spectral variance is proportional to the mass spectral intensity.

31. The method of claim 1, where the probability measure is a p-value.

32. The method of claim 1, where the overall probability measure is a product of individual p-values for all matching fragments within said ion.

33. The method of claim 1, where the candidate ions or fragments are generated based on one of a list and database of known proteins or peptides.

34. The method of claim 33, where one of a list or database of proteins or peptides has been computationally digested in sillico by simulating an effect of an enzyme, such as trypsin.

35. The method of claim 1, wherein the overall probability measure is used to rank candidate ions taken from one of a list and a database of known ions.

36. The method of claim 1, where the first candidate ion or fragment to be considered is the result of a search within possible candidates.

37. The method of claim 36, where possible candidates are fragments involving at least one of all possible amino acids in a protein or peptide.

38. The method of claim 37, where the at least one amino acids include possible chemical modifications.

39. The method of claim 38, where the possible modifications include one of oxidation, dehydration, phosphorylation, sulphation, and glycosylation.

40. The method of claim 1, further comprising using the overall probability measure to rank sequences of amino acids for the purpose of de novo sequencing.

41. The method of claim 40, further comprising using the amino acid sequences obtained for text search in one of a list or a database.

42. The method of claim 1, where the possible candidate ions or fragments are reduced through the use of accurate mass determination from a measured mass spectral response.

43. The method of claim 1, where the candidate ions or fragments to be considered are from a list of possible additions or deletions based on the ions or fragments previously considered.

44. The method of claim 43, where the additions or deletions are from a list of possible ions or fragments.

45. The method of claim 44, where the possible ions or fragments involve at least one amino acid in a protein or peptide.

46. The method of claim 45, where the at least one amino acid includes possible chemical modifications.

47. The method of claim 46, where the possible modifications include one of oxidation, dehydration, phosphorylation, sulphation, and glycosylation.

48. The method of claim 1, where the candidate ion or fragment is taken from a possible part of a polymer.

49. The method of claim 37, where the polymer is from a DNA molecule.

50. The method of claim 49, where a possible part of a polymer is modified by at least one of a list of possible modifications.

51. The method of claim 1, where the probability measure is used to assess one of presence, absence, and likelihood of an ion or fragment.

52. The method of claim 1, where the probability measure is used to rank a list of possible ions or fragments.

53. The method of claim 1, where the overall probability measure is used to assess one of the presence, absence, and likelihood of an ion.

54. The method of claim 1, where the overall probability measure is used to rank a list of possible ions.

55. The method of claim 1, where the peak component matrix is updated and regression repeated by adding or deleting components in the matrix.

56. The method of claim 55, where adding or deleting components is based on probability measures obtained from a regression.

57. The method of claim 1, where a mass spectral response includes a plasmagram in ion mobility spectrometry.

58. The method of claim 1, where the mass axis has been transformed through one of linear and nonlinear functions.

59. The method of claim 1 where the at least two ions are at least two satellite isotopes of the ion and the analysis of the ion is based on its mass spectrally resolved satellite isotopes.

60. The method of claim 59, where the at least two satellite isotopes include a monoisotope.

61. A computer programmed to perform the method of claim 1.

62. The computer of claim 61, in combination with a mass spectrometer for obtaining mass spectral data to be analyzed by said computer.

63. A computer readable medium having computer readable code thereon for causing a computer to perform the method of claim 1.

64. A mass spectrometer having associated therewith a computer for performing data analysis functions of data produced by the mass spectrometer, the computer performing the method of claim 1.

* * * * *